US010338310B2

(12) United States Patent
Lu et al.

(10) Patent No.: US 10,338,310 B2
(45) Date of Patent: Jul. 2, 2019

(54) LIGHT TRANSMITTABLE AND TISSUE INTEGRABLE BIOFIBER DEVICE

(71) Applicant: Luke Lu, San Diego, CA (US)

(72) Inventors: Luke Lu, San Diego, CA (US);
Michelle Lu, San Diego, CA (US);
Emily Lu, San Diego, CA (US);
Richard Lu, Chantilly, VA (US)

(73) Assignee: LUKE LU, San Diego, CA (US)

( * ) Notice: Subject to any disclaimer, the term of this patent is extended or adjusted under 35 U.S.C. 154(b) by 18 days.

(21) Appl. No.: 15/791,414

(22) Filed: Oct. 24, 2017

(65) Prior Publication Data
US 2019/0121024 A1     Apr. 25, 2019

(51) Int. Cl.
| A61B 5/00 | (2006.01) |
| G02B 6/04 | (2006.01) |
| G02B 6/12 | (2006.01) |
| G02B 6/24 | (2006.01) |
| G02B 6/122 | (2006.01) |

(52) U.S. Cl.
CPC .......... *G02B 6/1221* (2013.01); *A61B 5/0059* (2013.01); *G02B 6/04* (2013.01); *G02B 6/241* (2013.01); *G02B 2006/12069* (2013.01)

(58) Field of Classification Search
CPC .................................................... A61B 5/0059
See application file for complete search history.

(56) References Cited

U.S. PATENT DOCUMENTS

| 5,693,043 A * | 12/1997 | Kittrell | A61B 1/00096 606/15 |
| 2005/0259942 A1 * | 11/2005 | Temelkuran | A61B 18/201 385/147 |
| 2017/0328836 A1 * | 11/2017 | Lu | G01N 21/658 |

* cited by examiner

*Primary Examiner* — Sung H Pak
*Assistant Examiner* — Hoang Q Tran
(74) *Attorney, Agent, or Firm* — Leong C. Lei (57) ABSTRACT

The present invention provides a light transmittable and tissue integration integrable biofiber device including a plurality of biofibers. The plurality of biofibers consist a single bare fiber or a single constructed fiber. The single constructed fiber consists a core layer and either a single cladding layer or a plurality of cladding layers, and the cladding layer clads and fuses a circumferential surface of the core layer. Each of the plurality of biofibers comprises a light receiving end and a light emitting end, a light radiates through the light receiving end and the light is emitted from the a light emitting end. Therefore, the biofiber device of the present invention may simultaneously accomplish light transmittable and tissue integrable purposes to facilitate light therapy, optical gene therapy and optogenetics.

7 Claims, 7 Drawing Sheets

LIGHT TRANSMITTABLE AND TISSUE INTEGRABLE BIOFIBER DEVICE

(a) TECHNICAL FIELD OF THE INVENTION

The present invention relates to a biofiber device that allows light transmission and tissue integration, and more particularly to a medical device made of biofibers. It can be made into the following device: tube, rod, plate and suture implants.

(b) DESCRIPTION OF THE PRIOR ART

An optical fiber is an optical conduction tool, in which light is transmitted in a fiber made of a glass or plastics by means of an internal total reflection principle. As science and technology continue to advance, optical fiber is also used for medical purposes, such as endoscopy. Endoscopy is a soft and flexible tube, containing a plurality of optical fibers. When the endoscope passes through patient's mouth, nose, digestive tract and other internal organ changes of the internal organ of human body can be examined, reducing the risk of a surgery. Currently, endoscopy is performed to examine various internal organs of the human body and remove tissue for biopsy when necessary. However, the existing instrument cannot be integrated with human tissue and must be removed after the surgery.

Optical fiber is also used in light therapy, which uses sunlight or artificial light, such as infrared, ultraviolet or laser to treat symptoms of diseases. At present, a variety of diseases can be treated by the light therapy. However, the devices used these days in a light therapy are large instruments that cover larger target areas through means of external radiation method. Light is transmitted through the epidermal tissue, subcutaneous tissue and mucocutaneous of the skin and then to the tissue cells. Therefore, the exact amount of radiation absorbed by the skin cannot be measured accurately and the inconvenience of operating these equipments remains Additionally, in the existing laser light therapy technology, the endoscope connecting the optical fiber is inserted into the opening of the human body and the laser is radiated precisely on the tumor cells. During the treatment, energy is produced from the end of the optical fiber, killing the tumor cells. However, the existing treatment technique requires the optical fiber to be removed after the treatment and reinserted at the time of the next treatment. Therefore, the patient's discomfort and infection rate can be highly increased due to the repeated procedure of inserting and removing the optical fiber.

In order to eliminate the aforementioned problems, the inventor of the present application provides a biofiber device with light transmission. Therefore, the physicians or other professionals can clearly observe the internal organs of the human body or animals Furthermore, the inventor of the present application also provides a biofiber device capable of integrating with soft tissue and hard tissue; wherein the biofiber device can be integrated with the organism and does not result in any inflammatory reactions.

SUMMARY OF THE INVENTION

The main purpose of the present invention is to provide a light transmittable and tissue integrable biofiber device and allow light to be transmitted to the target cells. With the biofiber integrated in the tissue itself, light therapy can be performed at any desired time or location. In addition, the biofiber device provided in the present invention is made out of a bioactive or bioinert material glass fiber, both with or without X-ray opacity that offers integration between the biofiber device and hard tissue or soft tissue. This prevents inflammation responses when the biofiber device is inserted into the body.

To achieve the above object, the present invention provides a biofiber device comprising a plurality of biofibers with or without an adhesive polymer. First, the plurality of biofibers consisting a single bare fiber or a single constructed fiber. The single constructed fiber consist of a core layer and either a single cladding layer or a plurality of cladding layers with each layer cladded and fused a circumferential surface of the core layer. The shapes of the single bare fiber and the constructed fiber, the core layer and the cladding layer can be randomly varied based on the user's requirements and preferences. In a preferred embodiment of the present invention, the single bare fiber and the single constructed fiber are formed with a round, a hexagonal, or a strip filament. In this embodiment, the core layer can either be formed with a round or a hexagonal filament. The cladding layers are composed of round, hexagonal, or strip filaments, which enhance the strength of the woven fiber structure, but the present invention is not limited thereto.

The refractive index of the cladding layer is lower than that of the core layer. The coefficient of thermal expansion of the cladding layer is lower than that of the core layer. As for the single bare fiber and constructed single fiber can be made of either a bioactive or bioinert material glass fiber and with or without X ray opacity. Furthermore, the adhesive polymer can be made out of a thermoplastic, thermosetting, high temperature, pressure or biodegradable polymer, such as polylactic acid (PLA) and polylactide-co-glycolide (PLGA). Such adhesive polymer is provided within the plurality of biofibers. The adhesive polymer has an inner and outer wall and a body part located between the inner wall and the outer wall. The inner wall has a hollow passage and the plurality of biofibers are located in the body part. The material of the adhesive polymer of the present invention can be altered based on the user's preferences.

The plurality of fiber optics are intertwined with each other, resulting in an increased structural strength. The biofiber is a woven fiber structure comprised of a center fiber and many braided fiber shafts interlaced-knitted around the center fiber shaft. Additionally, each of the plurality of biofibers consists of a light receiving end and a light emitting end, in which light radiates through the light receiving end and emitted from the light emitting end. The biofiber device has a light receiving part and a light emitting part with the light receiving part made of the light receiving ends of biofibers and the light emitting part made of the light emitting ends of the biofibers.

Each of the plurality of biofibers is composed of a bioabsorbable material, a semi-bioabsorbable material or a non-bioabsorbable material. The bioabsorbable material may be released from the plurality of biofibers, contacting the soft and hard tissue for integration purposes. Therefore, the biofiber device of the present invention can be absorbed by the body and the occurrence of inflammation can be avoided in the meantime.

Made using the etching method, a well is formed on the core layer of the present invention. It is used for culturing cells, carrying chemicals or growing cells. The core layer, itself, has a hollow cylindrical channel, allowing light transmission.

The biofiber device has a hollow cylindrical channel running through the core layer, and the hollow cylindrical channel consists an entrance disposed on the light receiving end and an exit disposed on the light emitting end.

The plurality of cladding layers comprises a middle layer and a shell layer. The middle layer clads and fuses with the circumferential surface of the core layer, whereas the shell layer clads and fuses with that of the middle layer to form a multilayer single constructed fiber. The fiber materials of the core, middle and shell layer can be altered based on the user's requirements. They can be made with bioabsorbable, non-bioabsorbable or semi-bioabsorbable materials. Moreover, the treatment time of the disease can be controlled by the fiber material, resulting in different absorption levels of the core, middle, and shell layer.

Biofiber device can serve as a dental implant comprised of a fixture and a peripheral junction, in which the fixture can be used for osseointegrating bone of a jaw or skull and the peripheral junction can connect to the fixture, connecting an abutment and supporting a dental prosthesis.

The invention can also serve as a light transmittable rod or suture implant. The shapes of both implants are the same and the only difference can be found in their diameter. The diameter of the light transmittable rod implant is greater than that of the suture implant. Both of these implants can be located on the surface of a tumor cell. Light radiates through the light receiving part of the implant and is emitted on the tumor cell. In addition, the light transmittable suture implant can be used as a surgical suture for wound ligation, hemostasis suture and tissue integration. Since the light transmittable suture implant can be made of a bioabsorbable material, it can be degraded into a soluble product and absorbed in the human body or the animals. If made with a non-bioabsorbable material, the implants will not be degraded or absorbed in the human body or the animals. On the other hand, the semi-bioabsorbable material includes parts that can be absorbed or degraded in the human body and parts that cannot.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE PREFERRED EMBODIMENTS

In the following paragraphs, a detailed description is provided for a thorough understanding of the figures listed above. Well-known structures and devices will also be used schematically for better comprehension.

Figure 1:
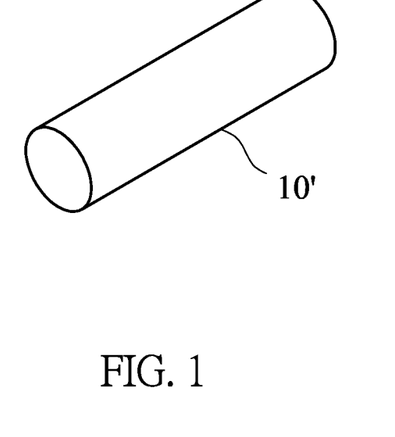
FIG. 1 is a stereoscopical schematic view of a single bare fiber according to the present invention.
Figure 2:
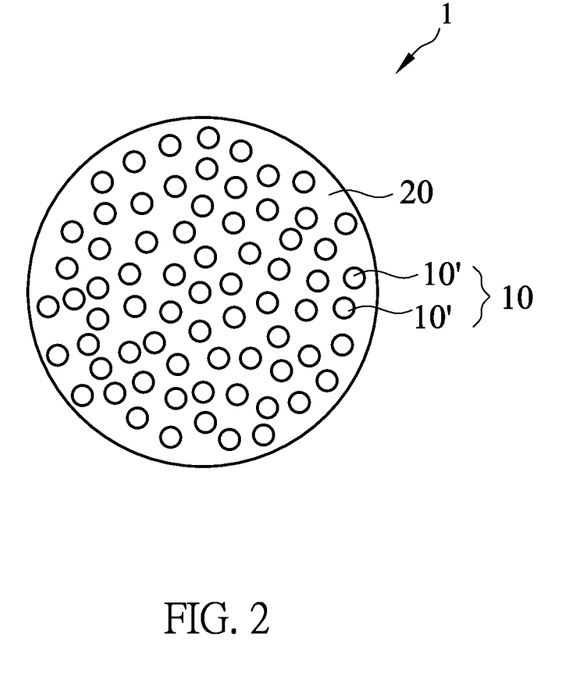
FIG. 2 is a cross-sectional schematic view of a plurality of single bare fibers with adhesive polymer according to the present invention.

As seen in FIG. 1 and FIG. 2, FIG. 1 is a stereoscopical schematic view of a single bare fiber according to the present invention; FIG. 2 is a cross-sectional schematic view of a plurality of single bare fibers with adhesive polymer according to the present invention. The light transmittable and tissue integrable biofiber device 1 comprises a plurality of biofibers 10 and an adhesive polymer 20, and each of the plurality of biofibers 10 is a single bare fiber 10'. The adhesive polymer 20, within the plurality of biofibers 10, is made out of thermosetting or biodegradable thermoplastic polymer.

Figure 3:
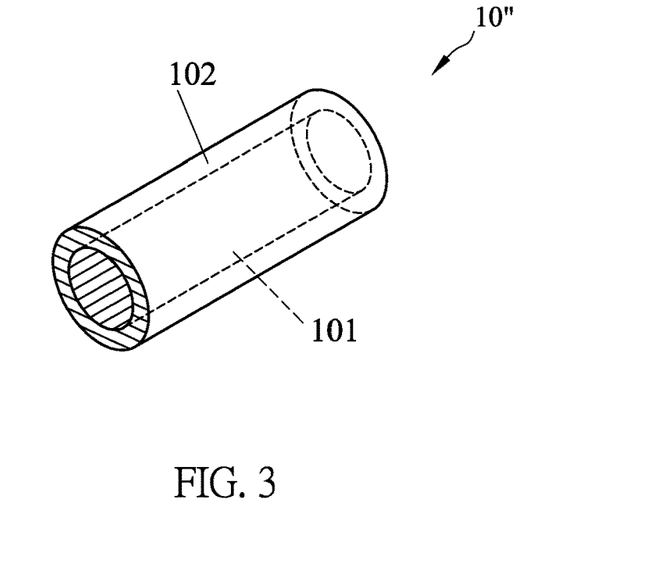
FIG. 3 is a stereoscopical schematic view of a single constructed fiber according to the present invention.
Figure 4:
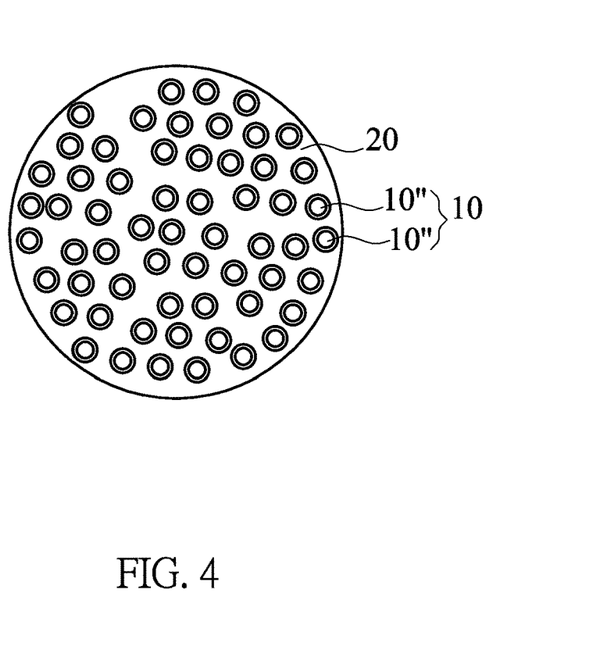
FIG. 4 is a cross-sectional schematic view of a plurality of single constructed fibers with adhesive polymer according to the present invention.

FIG. 3 is a stereoscopical schematic view of a single constructed fiber according to the present invention; FIG. 4 is a cross-sectional schematic view of a plurality of single constructed fibers with adhesive polymer according to the present invention. The plurality of biofibers 10 is a single constructed fiber 10", which consists a core layer 101 and a cladding layer 102. The cladding layer 102 clads and fuses with a circumferential surface of the core layer. The cladding layer 102 may be an inorganic (glass), organic resin or plastic. The adhesive polymer 20 can be provided within the single constructed fiber 10".

Figure 5:
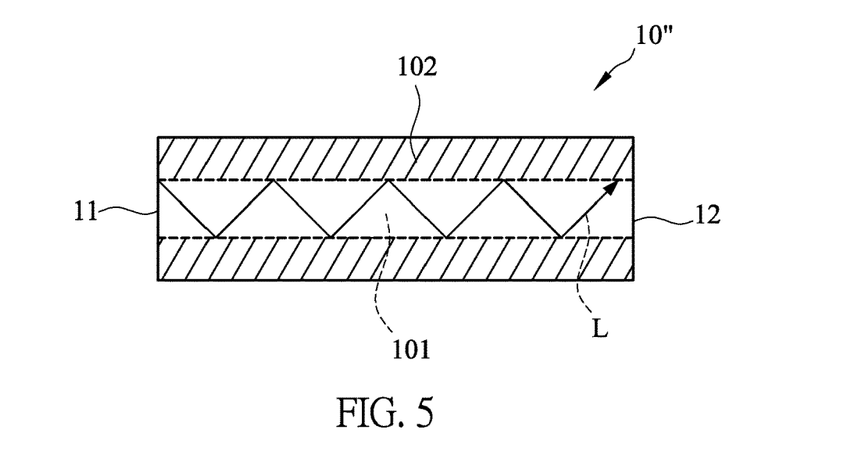
FIG. 5 is a schematic view of light traversing in the single constructed fiber according to the present invention.

FIG. 5 is a schematic view of light traversing in the single constructed fiber according to the present invention. The single constructed fiber 10" comprises a light receiving end 11 and a light emitting end 12. Light L radiates through the light receiving end 11 and is emitted from the light emitting end 12. Similarly, the biofiber device 1 also has a light receiving part and a light emitting part with both parts made out of a plurality of biofibers 10. The refractive indices and thermal expansion coefficients of all plurality of cladding layers 102 are lower than that of core layers' 101.

Figure 6A:
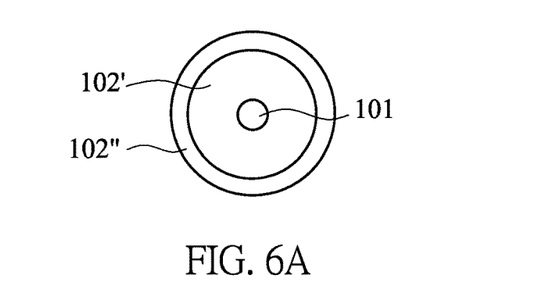
FIG. 6A is a cross-sectional schematic view of single constructed fiber according to a first embodiment of the present invention.
Figure 6B:
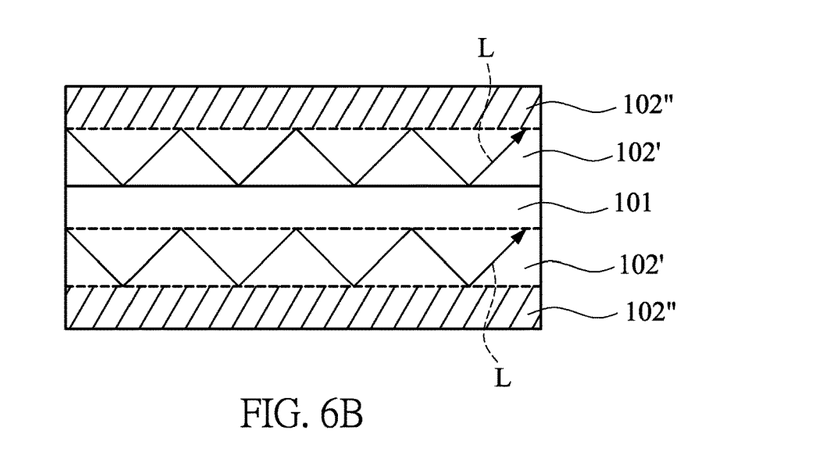
FIG. 6B is a schematic view of light traversing in the single constructed fiber according to a first embodiment of the present invention.

This is demonstrated in FIG. 6A and FIG. 6B. FIG. 6A is a cross-sectional schematic view of single constructed fiber according to a first embodiment of the present invention; and FIG. 6B is a schematic view of light traversing in the single constructed fiber according to a first embodiment of the present invention. Each of the plurality of biofibers 10 comprises the core layer 101 and the cladding layer 102. The cladding layer 102 comprises a middle layer 102' and a shell layer 102". The middle layer 102' clads and fuses a circumferential surface of the core layer 101, and the shell layer 102" clads and fuses a circumferential surface of the middle layer 102'. As shown in FIG. 6B, the light can be transmitted through the middle layer 102' when the light is not transmitted through the core layer 101. When the biofiber device 1 is used as a dental implant, phosphorus ions and calcium ions are released from the core layer 101 and crystallizes when react with collagen in the human body to form hydroxylapaite; therefore, the core layer 101 integrated with the bone does not have light transmittable effect. Hence, the light L can transmitted through the middle layer 102' disposed on the upper side and lower side of the core layer 10.

Figure 7:
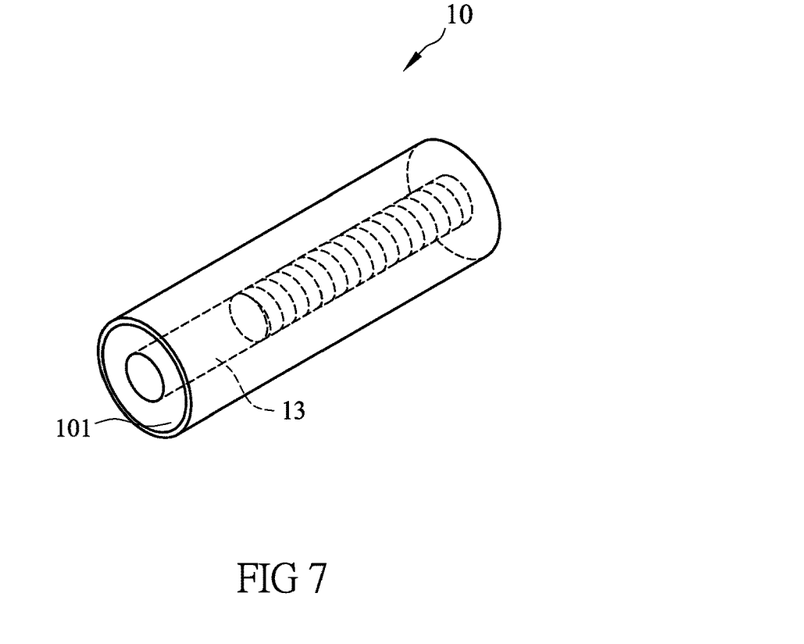
FIG. 7 is a stereoscopical schematic view of single constructed fiber according to a second embodiment of the present invention.

FIG. 7 is a stereoscopical schematic view of single constructed fiber according to a second embodiment of the present invention. Each of the plurality of biofibers 10 is made out of bioabsorbable material. The core layer 101 has a well 13 formed by an etching method. The well 13 is used for cell culturing, carriage and chemical carriage. During the treatment, the chemicals required for the patient are placed on well 13 and biofibers 10 is placed into the human body through an opening on the human body. When the chemical reaches the treatment site, the chemicals are released. Alternatively, the cultured cells on well 13 may be placed into the human body through an opening.

Figure 8:
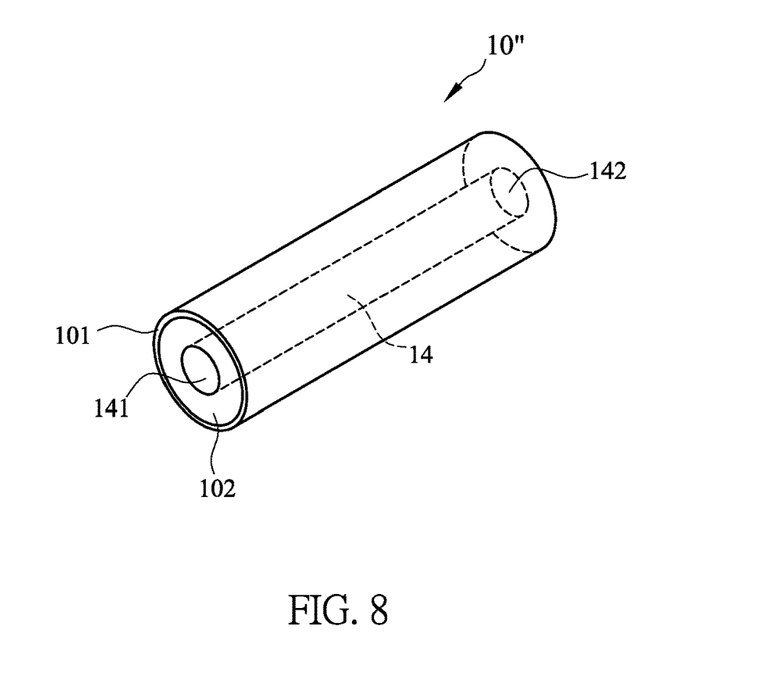
FIG. 8 is a stereoscopical schematic view of single constructed fiber according to a third embodiment of the present invention.

The details mentioned above applies to the single constructed fiber with the only difference that the core layer 101 has a hollow cylindrical channel 14. FIG. 8 is a stereoscopical schematic view of single constructed fiber according to a third embodiment of the present invention. The single constructed fiber 10" comprises a core layer 101 and the cladding layer 102. The core layer 101 has the hollow cylindrical channel 14 consists an entrance 141 disposed on the light receiving end and an exit 142 disposed on the light emitting end.

Figure 9A:
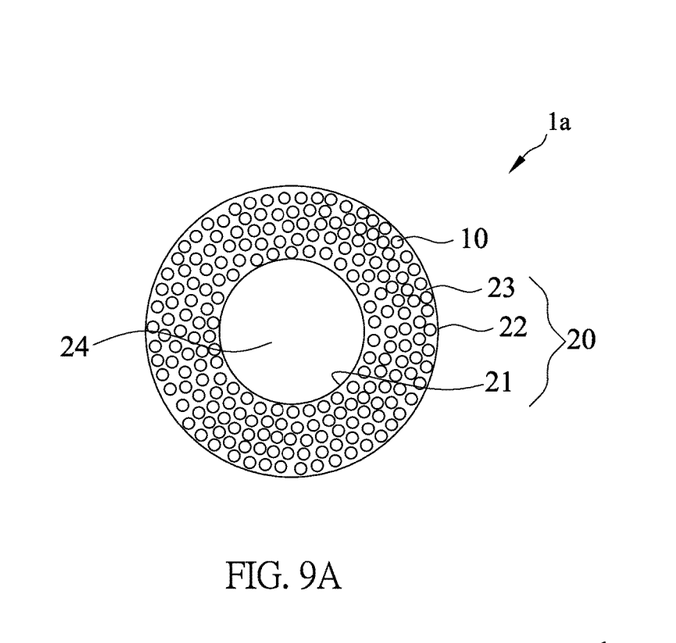
FIG. 9A is a cross-sectional schematic view of a light transmittable rod implant according to a fourth embodiment of according to the present invention.
Figure 9B:
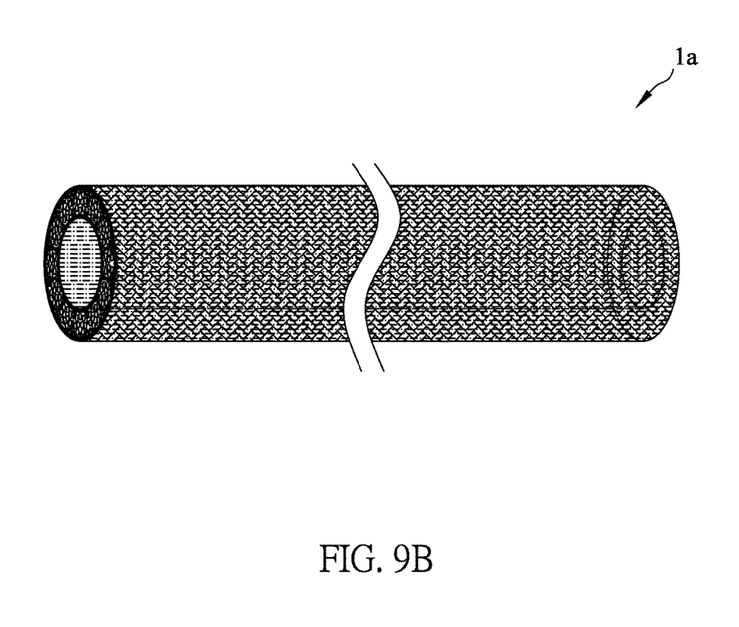
FIG. 9B is a stereoscopical schematic view of a light transmittable rod implant according to the fourth embodiment of according to the present invention.

FIG. 9A is a cross-sectional schematic view of a light transmittable rod implant according to a fourth embodiment of according to the present invention; and FIG. 9B is a stereoscopical schematic view of a light transmittable rod implant according to the fourth embodiment of according to the present invention. The biofiber device 1 is a light transmittable tube implant 1a comprising a plurality of biofibers 10 and an adhesive polymer 20. The adhesive polymer 20 has an inner wall 21, an outer wall 22 and a body part 23 disposed between the inner 21 and outer walls 22. The inner wall 21 encloses around to form a hollow passage 24, and the plurality of biofibers 10 are located in the body part 23. The light transmittable tube implant 1a can be used as a blood vessel or an intestine replacement that is no longer functioning properly. When the blood vessel of the organism is obstructed, light transmittable tube implant can be placed near the original blood vessel to allow normal blood flow in the organism.

Figure 10:
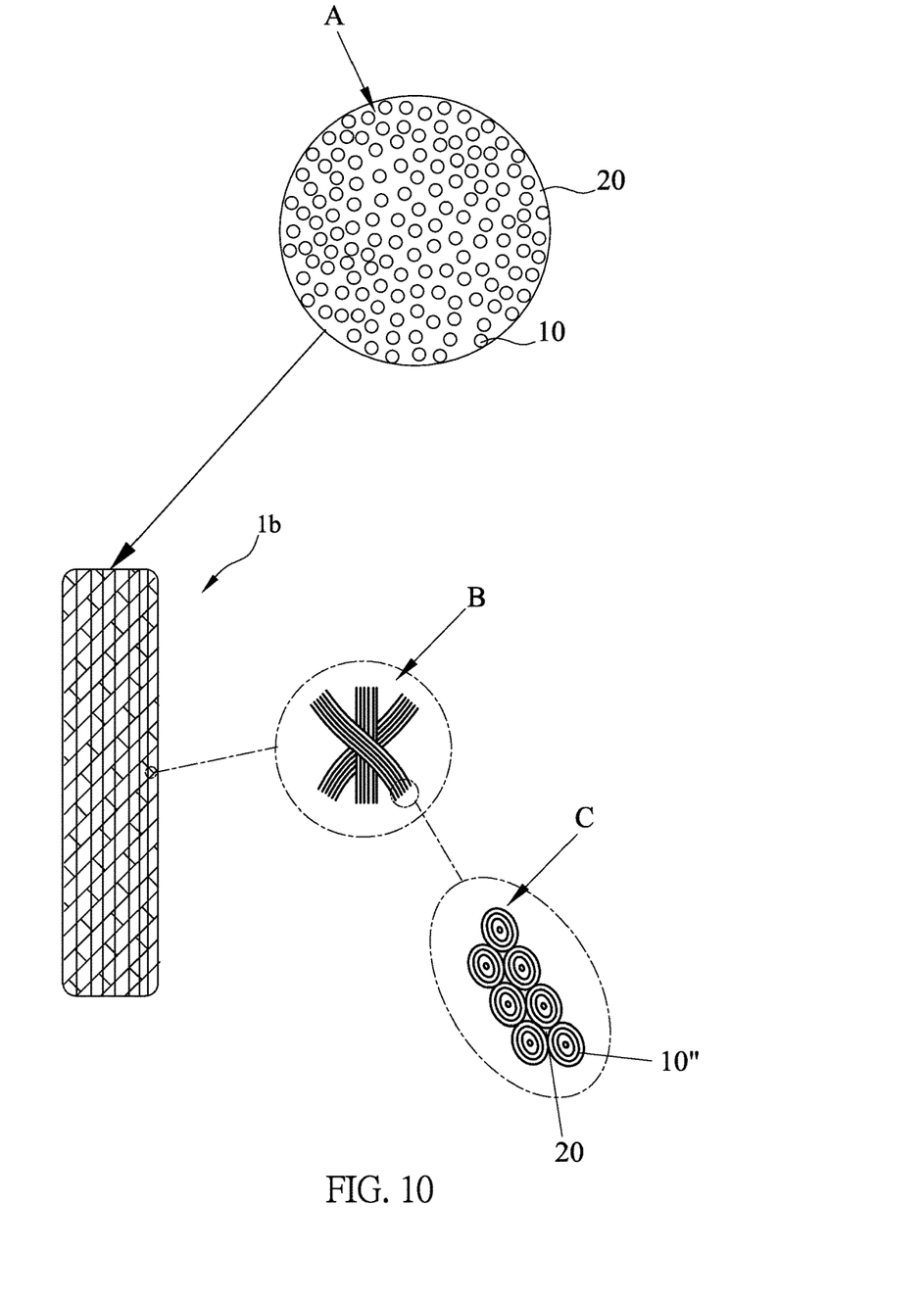
FIG. 10 is a schematic view of a light transmittable rod implant according to a fifth embodiment of according to the present invention.

FIG. 10 is a schematic view of a light transmittable rod implant according to a fifth embodiment of according to the present invention. The biofiber device is a light transmittable rod implant 1b comprising the biofibers 10 with the adhesive polymer 20. In sub-figure A of FIG. 10, the plurality of biofibers 10 are fixed within the adhesive polymer. This "*" pattern of sub-figure B provides an additional fixation for the braided fiber shafts and a higher tensile strength in vertical direction, and thus giving a more rugged structure in comparison to that of traditional structure with "x" pattern. Sub-figure C of FIG. 10 shows a section-enlarged view of the light transmittable rod implant 1b comprising the plurality of single constructed fibers 10" and adhesive polymer 20. Each of the single constructed fiber 10" is made out of the core layer and the plurality of cladding layers. The light transmittable rod implant 1b can be used for treating tumor cell. During the treatment, one end of the rod implant 1b is inserted into the tumor cells, and laser heat treating is applied to the other end of the optical fiber. Another light transmittable rod implant 1b is integrated within the epidermis of the human body to form a dot for light transmission. With that technology integrated, a patient can perform light therapy treatment through the dot at any time of the day at his/her own convenience via the use of a controller.

Figure 11:
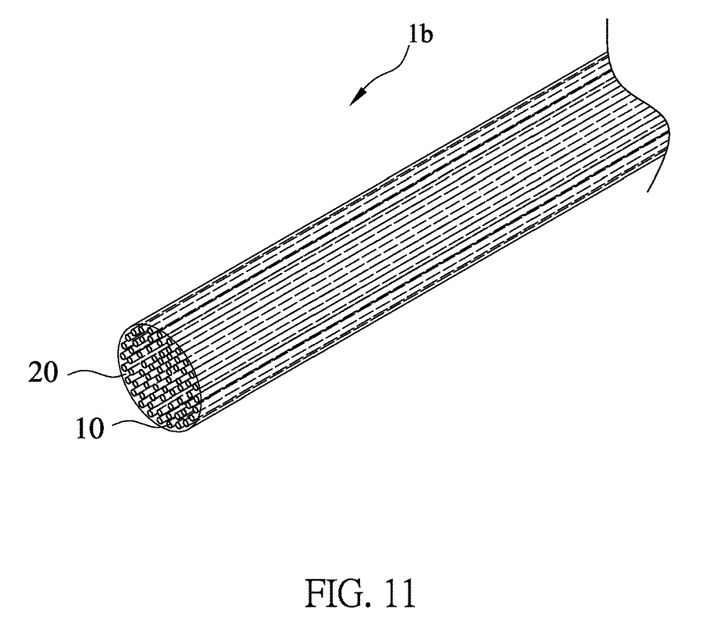
FIG. 11 is a stereoscopical schematic view of a light transmittable rod implant according to a sixth embodiment of according to the present invention.

The light transmittable rod implant structure is substantially the same as the one mentioned above with a slight change in structure. The plurality of biofibers mentioned previously has a woven fiber structure, but the plurality of biofibers in FIG. 11 are made up of biofiber filaments. In FIG. 11, the light transmittable rod implant 1b comprises the plurality of biofiber 10 filament. The plurality of biofibers 10 can be in single bare fibers or single constructed fibers with the adhesive polymer 20.

Figure 12:
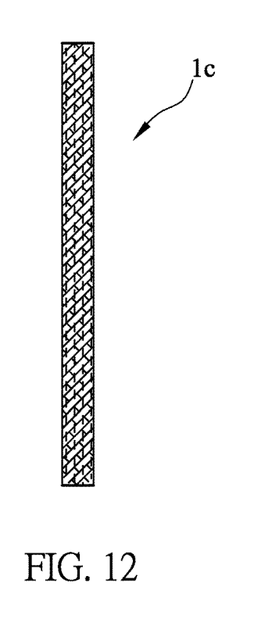
FIG. 12 is a schematic view of a light transmittable suture implant according to a seventh embodiment of according to the present invention.

FIG. 12 is a schematic view of a light transmittable suture implant according to a seventh embodiment of according to the present invention. The plurality of biofibers form a woven fiber structure, and the plurality of biofibers is either made out of single bare fibers or single constructed fibers. The light transmittable suture implant 1c can be used to treat tumor cell and can also be used as surgical or hemostasis suture for wound ligation and tissue integration. The light transmittable suture implant 1c is made out of bioabsorbable or semi-bioabsorbable material, in which the material can degrade and be absorbed by the human body.

Figure 13:
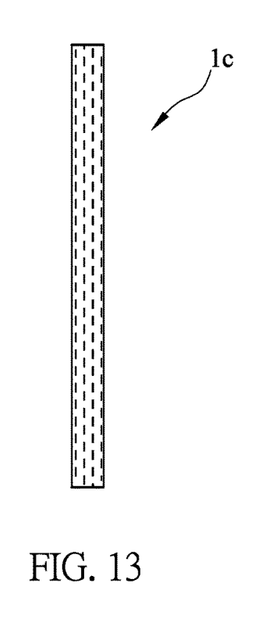
FIG. 13 is a schematic view of a light transmittable suture implant according to an eighth embodiment of according to the present invention.

FIG. 13 is a schematic view of a light transmittable suture implant according to an eighth embodiment of according to the present invention. The light transmittable suture implant 1c is made out of biofiber filaments with single bare fibers or the plurality of single constructed fibers.

The above descriptions for each figure explain the principles of the disclosure and its practical applications. The embodiments depicted above and the appended drawings are exemplary and are not intended to be exhaustive or to limit the scope of the disclosure. Modifications and variations are possible in view of the above teachings.

We claim:
1. A light transmittable and tissue integrable biofiber device, comprising:
   a plurality of biofibers consisting a single bare fiber or a single constructed fiber, the single constructed fiber consisting a core layer and either a single cladding layer or a plurality of cladding layers, the cladding layer cladding and fusing a circumferential surface around the core layer;
   wherein each of the plurality of biofibers comprises a light receiving end and a light emitting end, a light radiates through the light receiving end and the light is emitted from the light emitting end;
   wherein the biofiber device has a light receiving part and a light emitting part, and both the light receiving part and the light emitting part is made of plurality of biofibers;
   wherein the biofiber device further comprises an adhesive polymer provided within the plurality of biofibers, made out of a thermosetting polymer or a biodegradable thermoplastic polymer;
   wherein each of the plurality of biofibers is made of a bioabsorbable material, a semi-absorbable material or a non-bioabsorbable material;
   wherein a well is formed by an etching method in the core layer to allow cell culturing and chemical carriage; and wherein the biofiber is a woven fiber structure comprising a center fiber shaft and multiple braided fiber shafts interlaced-knitted around the center fiber shaft.

2. The biofiber device mentioned in claim 1, wherein the single bare fiber and constructed single fiber are made of either bioactive or bioinert material glass fiber and with or without X ray opacity.

3. The biofiber device mentioned in claim 1, wherein the biofiber device has a hollow cylindrical channel running through the core layer, and the hollow cylindrical channel consists an entrance disposed on the light receiving end and an exit disposed on the light emitting end.

4. The biofiber device mentioned in claim 1, wherein the plurality of cladding layers comprises a middle layer and a shell layer; the middle layer clads and fuses a circumferential surface of the core layer; the shell layer clads and fuses a circumferential surface of the middle layer to form a multilayer single constructed fiber; and the refractive indices of each cladding layers is lower than that of the core layers.

5. The biofiber device mentioned in claim 4, wherein the cladding layers in the biofiber device are made of bioactive or bioinert materials, and the layer of the single constructed fiber is made of bioactive material.

6. The biofiber device mentioned in claim 1, wherein the biofiber device is a light transmittable tube implant comprised of the plurality of biofibers with adhesive polymer; the adhesive polymer has an inner wall, an outer wall and a body part disposed between the inner and outer wall; and the inner wall encloses a hollow passage with plurality of biofibers located in the body part.

7. The biofiber device mentioned in claim 1, wherein the biofiber device is a light transmittable rod or a light transmittable suture implant located on the surface of a tumor cell; the light radiates through the light receiving part and is emitted from the light emitting part of the implant to reverse tumor cell growth.

* * * * *